(12) United States Patent
McCullough

(10) Patent No.: US 9,220,294 B2
(45) Date of Patent: Dec. 29, 2015

(54) METHODS AND DEVICES USING CANNABIS VAPORS

(71) Applicant: Timothy McCullough, Stillwater, MN (US)

(72) Inventor: Timothy McCullough, Stillwater, MN (US)

( * ) Notice: Subject to any disclaimer, the term of this patent is extended or adjusted under 35 U.S.C. 154(b) by 0 days.

(21) Appl. No.: 14/264,999

(22) Filed: Apr. 29, 2014

(65) Prior Publication Data

US 2015/0223515 A1    Aug. 13, 2015

Related U.S. Application Data

(60) Provisional application No. 61/938,577, filed on Feb. 11, 2014.

(51) Int. Cl.

| | |
|---|---|
| *A61M 16/00* | (2006.01) |
| *A24B 13/00* | (2006.01) |
| *A61M 11/04* | (2006.01) |
| *A61K 31/352* | (2006.01) |
| *B01D 11/00* | (2006.01) |
| *B05D 1/40* | (2006.01) |
| *A61M 15/00* | (2006.01) |

(52) U.S. Cl.
CPC .............. *A24B 13/00* (2013.01); *A61K 31/352* (2013.01); *A61M 11/041* (2013.01); *A61M 11/042* (2014.02); *B01D 11/00* (2013.01); *B05D 1/40* (2013.01); *A61M 15/002* (2014.02); *A61M 15/0028* (2013.01); *A61M 15/0045* (2013.01); *A61M 15/0066* (2014.02); *A61M 2207/00* (2013.01)

(58) Field of Classification Search
CPC .................................................... A61K 31/352
USPC ........................................ 424/725, 448, 449
See application file for complete search history.

(56) References Cited

U.S. PATENT DOCUMENTS

| | | | |
|---|---|---|---|
| 3,270,437 A | 9/1966 | Castillo et al. | |
| 4,543,275 A | 9/1985 | Akashi et al. | |
| 4,913,865 A | 4/1990 | Toyotama | |
| 5,095,921 A | 3/1992 | Losee et al. | |

(Continued)

FOREIGN PATENT DOCUMENTS

| | | |
|---|---|---|
| WO | WO-9409842 A1 | 5/1994 |
| WO | WO-0176768 A1 | 10/2001 |

(Continued)

OTHER PUBLICATIONS

Hazekamp et al. Evaluation of a Vaporizing Device (Volcano1) for the Pulmonary Administration of Tetrahydrocannabinol. Journal of Pharmaceutical Sciences.vol. 95, Issue 6, Apr. 24, 2006.*

(Continued)

*Primary Examiner* — Cachet Sellman
(74) *Attorney, Agent, or Firm* — Schwegman Lundberg & Woessner, P.A.

(57) ABSTRACT

A method of purifying at least one of THC and CBD from a cannabis-containing composition includes heating the cannabis-containing composition to a temperature sufficient to volatilize at least one of THC and CBD into a vapor and condensing the vapor on a substrate. A drug delivery cartridge includes a substrate coated with at least one of THC and CBD and configured to allow for passage of air through the cartridge to volatilize at least one of THC and CBD for inhalation by a user to induce a medicinal or therapeutic effect to the user.

21 Claims, 15 Drawing Sheets

(56) References Cited

U.S. PATENT DOCUMENTS

| | | | |
|---|---|---|---|
| 5,224,498 | A | 7/1993 | Deevi et al. |
| 5,269,327 | A | 12/1993 | Counts et al. |
| 5,878,752 | A | 3/1999 | Adams et al. |
| 5,935,388 | A | 8/1999 | Meszaros |
| 6,045,864 | A | 4/2000 | Lyons et al. |
| 6,095,153 | A | 8/2000 | Kessler et al. |
| 6,513,524 | B1* | 2/2003 | Storz ................... 128/203.26 |
| 6,589,395 | B1 | 7/2003 | Meili |
| 6,630,507 | B1 | 10/2003 | Hampson et al. |
| 6,909,839 | B2 | 6/2005 | Wang et al. |
| 7,025,992 | B2 | 4/2006 | Whittle |
| 7,088,914 | B2 | 8/2006 | Whittle et al. |
| 7,279,421 | B2 | 10/2007 | Suzuki |
| 7,344,736 | B2 | 3/2008 | Whittle et al. |
| 7,399,872 | B2 | 7/2008 | Webster et al. |
| 7,402,686 | B2 | 7/2008 | Duchek |
| 7,524,881 | B2 | 4/2009 | Goodwin et al. |
| 7,540,286 | B2 | 6/2009 | Cross et al. |
| 7,622,140 | B2 | 11/2009 | Whittle et al. |
| 7,651,570 | B2 | 1/2010 | Brcka |
| 7,674,922 | B2 | 3/2010 | Burdick et al. |
| 7,741,365 | B2 | 6/2010 | Makriyannis et al. |
| 8,034,843 | B2 | 10/2011 | Whittle et al. |
| 8,147,898 | B2 | 4/2012 | Coates et al. |
| 8,481,091 | B2 | 7/2013 | Ross |
| 8,512,767 | B2 | 8/2013 | Ross |
| 2002/0117175 | A1 | 8/2002 | Kottayil et al. |
| 2003/0221625 | A1 | 12/2003 | Toda et al. |
| 2004/0096402 | A1 | 5/2004 | Hodges et al. |
| 2004/0126326 | A1 | 7/2004 | Rabinowitz et al. |
| 2004/0138293 | A1 | 7/2004 | Werner et al. |
| 2004/0147767 | A1* | 7/2004 | Whittle et al. ............... 549/390 |
| 2005/0042172 | A1* | 2/2005 | Whittle ........................ 424/46 |
| 2005/0063686 | A1* | 3/2005 | Whittle et al. ............... 392/390 |
| 2006/0039959 | A1 | 2/2006 | Wessling |
| 2006/0160888 | A1 | 7/2006 | Kottayil et al. |
| 2006/0167084 | A1 | 7/2006 | Dudley |
| 2007/0020193 | A1 | 1/2007 | de Vries et al. |
| 2007/0041994 | A1 | 2/2007 | McDowell |
| 2007/0049645 | A1 | 3/2007 | Mechoulam et al. |
| 2007/0099987 | A1 | 5/2007 | Weiss et al. |
| 2008/0057117 | A1 | 3/2008 | Werner et al. |
| 2008/0181942 | A1 | 7/2008 | Zajicek |
| 2008/0216828 | A1 | 9/2008 | Wensley et al. |
| 2008/0255224 | A1 | 10/2008 | Blum |
| 2008/0262099 | A1 | 10/2008 | Whittle et al. |
| 2008/0275237 | A1 | 11/2008 | Arslantas et al. |
| 2008/0306285 | A1 | 12/2008 | Hale et al. |
| 2009/0005461 | A1 | 1/2009 | Nagarkatti et al. |
| 2009/0197941 | A1 | 8/2009 | Guy et al. |
| 2009/0324797 | A1 | 12/2009 | Bobzin et al. |
| 2010/0012118 | A1* | 1/2010 | Storz ................... 128/203.15 |
| 2010/0119606 | A1 | 5/2010 | Whittle |
| 2010/0158973 | A1 | 6/2010 | Weiss et al. |
| 2010/0204312 | A1 | 8/2010 | McAllister et al. |
| 2010/0204443 | A1 | 8/2010 | Gazit et al. |
| 2010/0239635 | A1 | 9/2010 | McClain et al. |
| 2010/0239693 | A1 | 9/2010 | Guy et al. |
| 2010/0249223 | A1 | 9/2010 | Di Marzo et al. |
| 2011/0052694 | A1 | 3/2011 | Stinchcomb et al. |
| 2011/0071178 | A1 | 3/2011 | Makriyannis et al. |
| 2011/0073120 | A1 | 3/2011 | Adamic |
| 2011/0082195 | A1 | 4/2011 | Guy et al. |
| 2011/0097283 | A1 | 4/2011 | Van Damme et al. |
| 2012/0304990 | A1 | 12/2012 | Todd |
| 2012/0311744 | A1 | 12/2012 | Sirkowski |
| 2013/0087144 | A1 | 4/2013 | Todd |
| 2013/0178453 | A1 | 7/2013 | Rohde et al. |
| 2013/0196960 | A1 | 8/2013 | Rohde et al. |
| 2013/0255702 | A1 | 10/2013 | Griffith, Jr. et al. |
| 2013/0276799 | A1 | 10/2013 | Davidson et al. |
| 2014/0060554 | A1 | 3/2014 | Collett et al. |
| 2015/0136158 | A1 | 5/2015 | Stevens et al. |
| 2015/0223523 | A1 | 8/2015 | Mccullough |

FOREIGN PATENT DOCUMENTS

| | | |
|---|---|---|
| WO | WO-2008/134668 A2 | 11/2008 |
| WO | WO-2010/111232 A9 | 3/2011 |
| WO | WO-2013083631 A1 | 6/2013 |
| WO | WO-2013/164761 A1 | 11/2013 |
| WO | WO-2015123064 A1 | 8/2015 |
| WO | WO-2015123317 A1 | 8/2015 |

OTHER PUBLICATIONS

"Big Pharma's Weed Winner", [online]. The Daily Beast, [retrieved on Apr. 29, 2014]., Retrieved from the Internet: <URL: http://www.thedailybeast.com/articles/2014/01/24/how-one-pharmaceutical-company-could-become-the-safest-and-most-trusted-of-all-cannabis-dealers.html#url=/articles/2014/01/24/how-one-pharmaceutical-company-could-become->, Jan. 24, 2014), 2 pgs.

"Decarboxylating Cannabis: Turning THCA into THC", [online}. [retrieved on Apr. 29, 2014]. Retrievefd from the Internet: <URL: http://www.marijuanagrowershq.com/decarboxylating-cannabis-turning-thca-into-thc/>, (Aug. 14, 2012), 36 pgs.

"Decarboxylation of cannabis: scientific info about temps and times", [online]. [archived on Jul. 5, 2013]. Retrieved from the Internet: <URL: http://cannabischris.com/2012/10/decarboxylation-of-cannabis/>, (Oct. 31, 2012), 5 pgs.

"Evaluation of Volcano(r) Vaporizer for the Efficient Emission of THC, CBD, CBN and the Significant Reduction And/Or Elimination of Polynuclear-Aromatic (PNA) Analytes Resultant of Pyrolysis", prepared by Chemic Laboratories, Canton, MA [online}. [retrieved on Apr. 29, 2014 . Retrieved from the Internet: <URL: http://www.maps.org/mmj/vaporizerstudy4.15.03.pdf>, (2003), 57 pgs.

"Hash Oil", [online]. [retrieved on Apr. 29, 2014]. Retrieved from the Internet: <URL: http://en.wikipedia.org/wiki/Hash_oil>, (last modified on Apr. 27, 2014), 4 pgs.

"Sativex®", [online], © 2014 GW Phamaceuticals. [retrieved on Apr. 29, 2014]. Retrieved from the Internet: <URL: http://gwpharm.com/Sative.aspx>, (2014), 2 pgs.

"Total Sublimation—Sublimator in Action", [online]. [retrieved on Apr. 29, 2014]. Retrieved from the Internet: <URL: http://thehighcanadian.wordpress.com/tag/total-sublimation/>, (2014), 3 pgs.

"Vacuum and fractional distillation", [online]. [retrieved on Apr. 29, 2014]. Retrieved from the Internet: <URL: http://boards.cannabis.com/concentrates/182951-vacuum-fractional-distillation.html>, (2014), 5 pgs.

"Vaporizer (inhalation device)", [online], Wikipedia®, the free encyclopedia, [retrieved on Apr. 29, 2014]. Retrieved from the Internet: <URL: http://en.wikipedia.org/wiki/Vaporizer_(inhalation_device)>, (modified on Mar. 21, 2014), 4 pgs.

"Volcano Vaporizer", [online]. © 2013 Storz & Bickel GMBH & Co. KG. [retrieved on Dec. 10, 2013]. Retrieved from the Internet: <URL: http://volcanovaporizer.com/about/>, (2013), 4 pgs.

"Volcano® Vaporization System". [online]. [retrieved on May 15, 2014]. Retrieved from the Internet: <URL: http://www.storz-bickel.com/vaporizer/volcano-technology.html>, (2014). 4 pgs.

"Why Vaporize?". [online]. © 2013 Storz & Bickel GMBH & Co, KG. [retrieved on Dec. 10, 2013], Retrieved from the Internet: <URL: http://volcanovaporizer.com/why-vape/>, (2013), 4 pgs.

Welch, William M., "Vaporizers, e-cigs of the pot world, are booming", [online]. USA Today. [retrieved on Apr. 29, 2014]. Retrieved from the Internet: <URL: http://www.usatoday.com/story/money/business/2014/03/15/marijuana-vapporizing-gains/6042675/>, (Mar. 17, 2014), 6 pgs.

"Amazon.com: EZ Breathe Atomizer Asthmalnhalers, Model # EZ100: Health & Personal Care", [Online]. Retrieved from the Internet: <URL: http://www.amazon.com/EZ-Breathe-Atomizer-Asthma-Inhalers-EZ-100/dp/B00DQSTVRQ/ref=pd_sxp_f_pt>, (Accessed: Mar. 3, 2015), 25 pgs.

"Tutorial: Atomizer vs. Cartomizer vs. Clearomizer Overview of Atomizer vs. Cartomizer vs. Clearomizer", [Online]. Retrieved from the Internet: <URL: https://www.misthub.com/blog/tutorialatomizervsclearomizer/>, (Accessed: Mar. 3, 2015), 15 pgs.

(56) References Cited

OTHER PUBLICATIONS

"Alexza Pharamaceuticals: Staccato Platform Details", [Online]. Retrieved from the Internet: <URL: http://www.alexza.com/staccato/staccato-platform>, (Accessed on: Jun. 30, 2015), 5 pgs.

"U.S. Appl. No. 14/574,591, Response filed Jun. 30, 2015 to Restriction Requirement mailed May 21, 2015", 9 pgs.

"U.S. Appl. No. 14/574,591, Restriction Requirement mailed May 21, 2015", 5 pgs.

"History: GW Pharmaceuticals", [Online]. Retrieved from the Internet: <URL: http://www.gwpharm.com/history.aspx>, (Accessed on: Jun. 30, 2015), 5 pgs.

"International Application Serial No. PCT/US2015/014418, Invitation to Pay Additional Fees and Partial Search Report mailed Apr. 20, 2015", 2 pgs.

"International Application Serial No. PCT/US2015/015445, International Search Report mailed May 14, 2015", 4 pgs.

"International Application Serial No. PCT/US2015/015445, Written Opinion mailed May 14, 2015", 16 pgs.

"JUJU Joints: Home page", [Online]. Retrieved from the Internet: <URL: http://jujujoints.com/>, (Accessed on: Jun. 30, 2015), 1 pg.

"JUJU Joints: The Deets", [Online]. Retrieved from the Internet: <URL: http://jujujoints.com/deets/>, (Accessed on: Jun. 30, 2015), 3 pgs.

"Open Vape-Products: O.Penvape Battery & Charger", [Online]. Retrieved from the Internet: <URL: http://www.openvape.com/shop/shop/featured-products/o-penvape-battery.html?SID=h9susctdi7uc88huscks6je2o0>, (Accessed on: Jun. 30, 2015), 3 pgs.

"Open vape: Home page", [Online]. Retrieved from the Internet: <URL: http://www.openvape.com/>, (Accessed on: Jun. 30, 2015), 2 pgs.

Chanbers, Rachel, "Leafly: What is Dabbing and How Do Dabs Work?", [Online]. Retrieved from the Internet: <URL: https://www.leafly.com/news/cannabis-101/is-dabbing-good-or-bad-or-both>, (Oct. 28, 2013), 9 pgs.

Hazekamp, Arno, "", Cannabis Extracting the Medicine Hazekamp Thesis, (2007), 187 pgs.

Mechoulam, Raphael, "Veterans for medical cannabis access: General use of cannabis for PTSD Symptoms", [Online]. Retrieved from the Internet: <URL: http://veteransformedicalmarijuana.org/content/general-use-cannabis-ptsd-symptoms>, (2010), 3 pgs.

Whittle, G. W, et al., "Prospect for new cannabis-based prescription medicines", Journal of Cannabis Therapeutics 3(4), (2001), 133-152.

"7 Things You Need to Know About Sativex", LeafScience, http://Imleafscience.com/2014/03/08/7-things-need-know-sativex/, (Mar. 8, 2014), 13 pgs.

"U.S. Appl. No. 14/574,591, Non Final Office Action mailed Aug. 18, 2015", 14 pgs.

"How to Use Your Inhaler", Asthma Society of Canada, [Online]. Retrieved from the Internet: <URL: http://asthma.ca/adults/treatment/spacers.php, (Oct. 2015), 3 pgs.

"International Application Serial No. PCT/US2015/014418, International Search Report mailed Jun. 25, 2015", 4 pgs.

"International Application Serial No. PCT/US2015/014418, Written Opinion mailed Jun. 25, 2015", 8 pgs.

"U.S. Appl. No. 14/574,591, Response filed Oct. 30, 2015 to Non Final Office Action mailed Aug. 18, 2015", 44 pgs.

\* cited by examiner

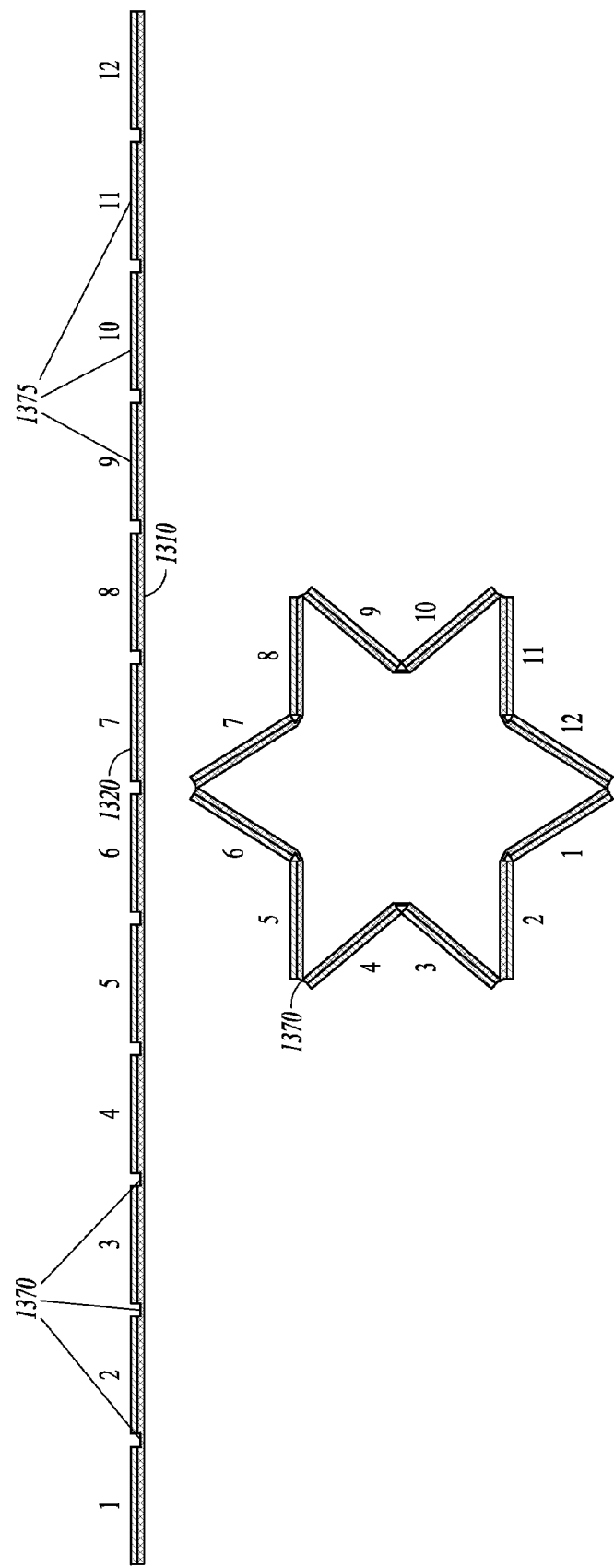

METHODS AND DEVICES USING CANNABIS VAPORS

CLAIM OF PRIORITY

This patent application claims the benefit of priority, under 35 U.S.C. Section 119(e) of McCullough, U.S. Provisional Patent Application Ser. No. 61/938,577, entitled "Methods and Devices Using Cannabis Vapors," filed on Feb. 11, 2014, which is hereby incorporated by reference herein in its entirety.

TECHNICAL FIELD

The present application relates to methods and devices using cannabis, and more particularly, to methods of purifying at least one of THC and CBD from cannabis to create drug delivery products containing THC or CBD.

BACKGROUND

Cannabis, otherwise known as marijuana, is a naturally occurring plant with at least two well-known pharmacologically active components, tetrahydrocannabinol (THC) and cannabidiol (CBD). When ingested, THC and CBD can provide numerous benefits and can be used, for example, to alleviate pain, muscle spasticity and in the treatment of nausea associated with chemotherapy.

Smoking of the cannabis material is a common form of THC and CBD ingestion. However, while THC and CBD are released by smoking, combustion of the cannabis material can also release many toxic substances such as ammonia and hydrogen cyanide that can cause damage if ingested. Ingestion of foods laced with cannabis material can deliver THC and CBD to the body. However, any other undesirable materials in the cannabis are also ingested and the dosage of THC and CBD can be inconsistent and hard to determine.

Isolation and purification of THC and CBD from cannabis can be of great interest and benefit to the medical community. A way to purify THC and CBD from cannabis and convert the purified THC and CBD into an easily-ingestible form is desired.

Goals of the Invention

There is an opportunity for a drug delivery product that allows for inhalation of at least one of THC and CBD without inhaling other undesirable components found in raw cannabis or created by burning the raw cannabis. The amount and purity of THC or CBD in the drug delivery product can be controlled for dosage. The drug delivery product can be formed using a separation and coating process, as described herein, that facilitates controlled deposition of THC or CBD onto a substrate to form the drug delivery product.

SUMMARY OF THE INVENTION

The at least one present invention is directed to methods for purifying tetrahydrocannabinol (THC) and cannabidiol (CBD) from cannabis plant material; providing substrates containing or incorporating the purified THC and CBD; and providing apparatuses for delivery of at least one of THC and CBD to patients and consumers.

In a first aspect of the invention, the method is directed to controlled volatilization of at least one of THC and CBD from preferably comminuted cannabis plant material and absorption, deposition, adsorption or otherwise condensing the volatilized THC or CBD or both on a substrate held at a temperature to assure capture of the volatilized THC, CBD or both.

A second aspect of the invention is directed to the substrate with deposited THC, CBD or both. The substrate with THC, CBD or both is constructed and configured to enable release of the THC, CBD or both upon controlled heating. This aspect can include controlled release of the THC, CBD or both so as to provide regulated, controlled, limited doses of THC, CBD or both over time. In a third aspect of the invention, the substrate with deposited THC, CBD or both is converted into a drug delivery cartridge. The drug delivery cartridge can be used with a controllable heating element to volatilize and inhale the THC, CBD or both.

BRIEF DESCRIPTION OF THE DRAWINGS

In the drawings, which are not necessarily drawn to scale, like numerals may describe similar components in different views. Like numerals having different letter suffixes may represent different instances of similar components. The drawings illustrate generally, by way of example, but not by way of limitation, various embodiments discussed in the present document.

FIG. 13C is a side view of the coated substrate of the drug delivery cartridge of FIGS. 13A and 13B prior to forming the polygonal shape.

DETAILED DESCRIPTION

Figure 1:
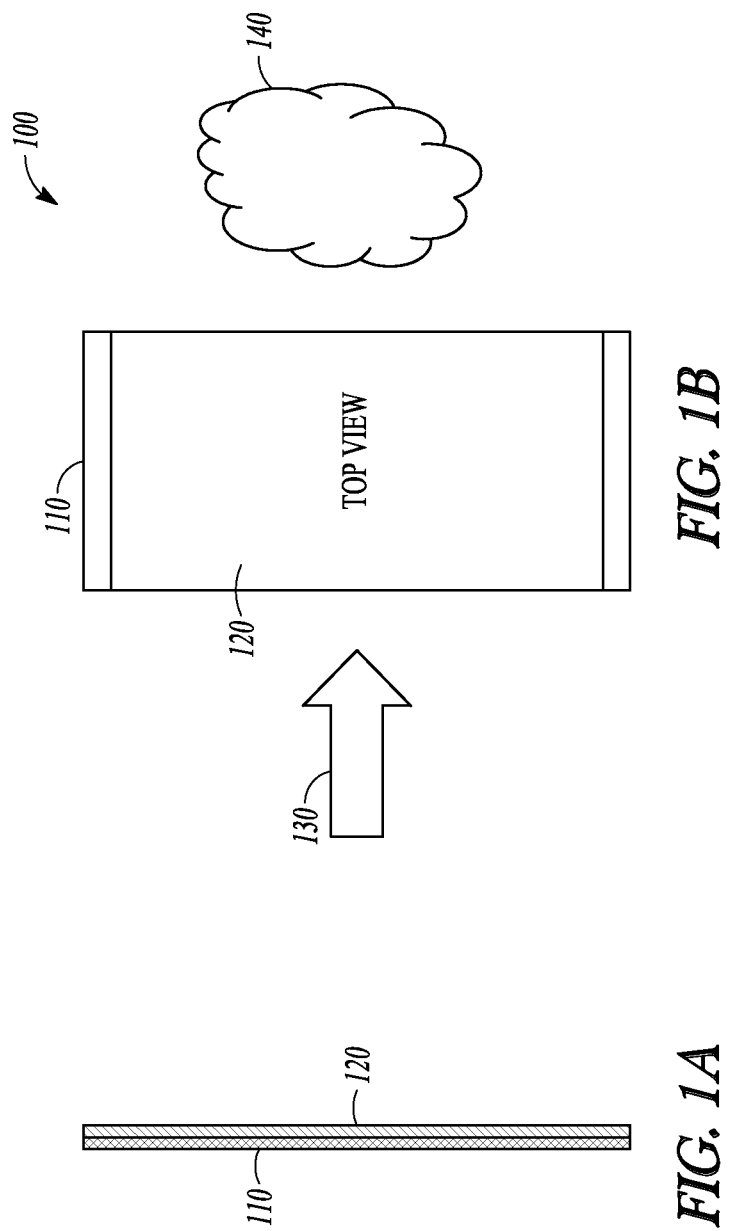
FIG. 1A is a side view of an example of a drug coated substrate in accordance with the present patent application.
FIG. 1B is a top view of the drug coated substrate of FIG. 1A.

The present application relates to methods of purifying at least one of THC and CBD from cannabis-containing compositions by heating the cannabis-containing compositions to vaporize at least one of THC and CBD and condensing the vapor onto a substrate to form a coated substrate comprising at least one of THC and CBD. The coated substrates can be converted into various three-dimensional structures configured for use as a drug delivery cartridge. The drug delivery cartridge can be heated up and air can pass through the cartridge, thus volatilizing the THC or CBD in the drug delivery cartridge such that the user can inhale the THC or CBD for a medicinal or therapeutic effect. The purity and ratios of THC and CBD in the drug delivery cartridge can be controlled based on the desired composition, and the quantities of THC and CBD can be controlled based on the desired dosage. Based on the process used to form the coated substrates, undesirable components in the cannabis are not included in the drug delivery cartridge. The drug delivery cartridges described herein can be used with various types of drug delivery devices to aid in inhalation of the THC or CBD.

As used herein, volatilize or volatilization can refer to vaporization of a component from a starting phase, either a liquid or a solid, to a gas phase. In an example, one or more components described herein may start as a solid and be heated such that the one or more components vaporize. The one or more components may transition directly from the solid to the gas phase, a sublimation process, or the one or more components may become a liquid and then vaporize to a gas. In an example, the one or more components described herein may be in a liquid form prior to heating. FIGS. 1A and 1B show side and top views of an example of a drug coated substrate 100 of the present disclosure. The drug coated substrate 100 can include a substrate component 110 onto which a drug component 120 can be deposited. The drug coated substrate 100 can be exposed to heated air 130, and the drug component 120 can be volatilized and entrained in the heated air 130 to form a heat released drug or HRD 140. The HRD 140 can then be ingested by a user to induce a medicinal or therapeutic effect on the user.

The substrate component 110 can be constructed from any naturally-occurring material or any man-made material, such as an FDA-approved polymer for the delivery of drugs, or any combination of naturally-occurring or man-made materials. The material selected for the substrate component 110 is inert at the heating temperatures described below for forming the coating on the substrate and the heating temperatures for later inhaling the one or more drug components from the coated substrate. In an example, the substrate component 110, can include, but is not limited to, materials where the substrate component 110 can be elastic, flexible, resilient, permanently deformable or plastically deformable.

In an example, the substrate component 110 can assume the form of any three dimensional structure, including, but not limited to, a sheet, a mesh, or any combination of three dimensional structures. Other types of structures can be employed without departing from the present subject matter. In an example, the substrate component 110 can be a sheet of polymer material. In an example, the substrate component 110 can be a sheet of aluminum mesh, a sheet of solid aluminum or a combination of both aluminum mesh and aluminum sheet. As used herein, the term aluminum can include all grades of aluminum and aluminum alloys. Materials suitable for use as the substrate component 110 are also described below in reference to FIG. 3.

As described further below, the substrate component 110 can be formed into a variety of three-dimensional shapes to form a drug delivery cartridge. In an example, the drug delivery cartridge can be designed to maximize the surface area of the drug component 120 exposed to the flow of heated air 130. In an example, the substrate component 110 can be shaped into forms including, but not limited to, a cone, a tube or tubular structure. As used here, a tubular structure can include any structure with an open cross-sectional area shape, a closed cross-sectional area shape, or a combination of open and closed cross-sectional area shapes. In an example, the cross-sectional area shapes can include, but are not limited to, circles, ovals, ellipses, squares, rectangles or other polygonal shapes. In an example, the cross-sectional area shapes can be open or closed shapes. Other types of structures can be employed without departing from the present subject matter.

The drug component 120 can include any volatilizable chemical or chemicals present in a raw material or a man-made material. In an example, the drug component 120 can include one or more active components for medicinal purposes or therapeutic effect. In an example, the drug component 120 can include one or more chemicals found in raw cannabis, including tetrahydrocannabinol, otherwise known as THC, or cannabidiol, otherwise known as CBD.

Cannabis material can exist in at least three distinct forms including, but not limited to, stem, resin (or hashish) and oil (or hash oil). In an example, the stem can include raw cannabis components such as stalks, leaves and flowers. As used herein, raw cannabis can refer to cannabis material that has been harvested but is otherwise unprocessed. In an example, the stem material can be shredded or chopped to increase the surface area of the stem material in preparation for purification. In an example, the resin can include kief, or the small particles of stem material that can be separated from the stem material by mechanical forces such as shaking. In an example, the kief can be compressed to form a solid for storage and later can be shredded or chopped to increase the surface area of the kief in preparation for purification. In an example, the oil can be obtained by solvent extraction treatments. Multiple references are made herein to starting with raw cannabis; it is recognized that any cannabis-containing composition can alternatively be used in the descriptions and examples below. Some of the processing steps, such as the separation or purification step, may vary depending on whether raw cannabis or an alternative form of a cannabis-containing composition is used.

Figure 2:
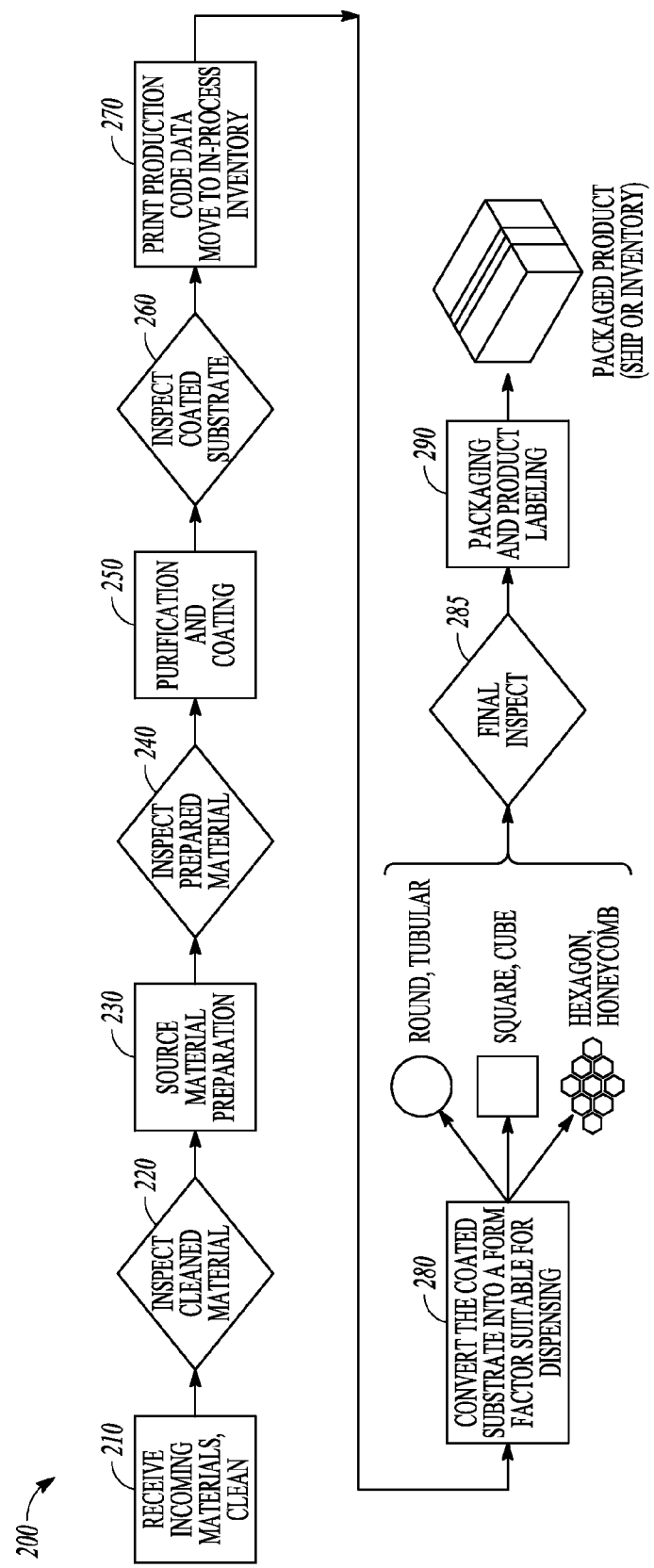
FIG. 2 is a block diagram of an example of a process for making a drug delivery cartridge in accordance with the present patent application.

FIG. 2 shows an example of a process 200 that can be used to form a drug delivery product, also referred to herein as a drug delivery cartridge. In an example, the drug delivery product includes at least one of THC and CBD. In the process 200, a pre-processing step 210 can include receiving source material, such as, for example, raw cannabis. In an example, the pre-processing step 210 can include collection of raw material from certified growers for use as source material and removal of undesirable organic and inorganic components from the source material. In an example, the source material can be a whole cannabis plant including the buds, leaves and stem.

A first inspection step 220 can include examination of the source material for general suitability in the process 200. In an example, source material that is diseased or not otherwise of a specified quality can be removed from the source material before further processing.

A source material preparation step 230 can further prepare the source material for later steps in the process 200. In an example, the source material preparation step 230 can include the use of equipment and methods to increase the surface area of the source material, such as by shredding or chopping, to aid in a purification process.

A second inspection step 240 can include examination of source material to ensure that the source material has been suitably processed. In an example, source material that has been improperly shredded or chopped may be rejected or redirected for further processing.

A purification and coating step 250 can include a process for separating the chemicals used to form the drug component 120 of FIG. 1 from the source material. In an example, the source material is raw cannabis and the one or more chemicals used to form the drug component 120 include at least one of THC and CBD. The purification in step 250 can include heating a cannabis-containing composition to volatilize at least one of THC and CBD from the cannabis-containing composition. Specific steps can depend on the form of the cannabis-containing composition. Under step 250, the volatilized chemicals can then be condensed onto a carrier material to form a drug coated substrate. In an example, the condensation of volatilized chemicals on a carrier material can be through absorption or adsorption of the volatilized chemicals.

A third inspection step 260 can include examination of the drug coated substrate for coating uniformity or other predetermined parameters.

A first post-processing step 270 can include identification and handling of the drug coated substrate. In an example, the drug coated substrate can be marked or labeled for quality assurance and material handling purposes, such as delivery of the drug coated substrate to inventory. In an example, steps 260 and 270 can be skipped and the coated substrate from step 250 can go directly to step 280 for converting.

A conversion step 280 can include transforming the drug coated substrate into form factors convenient for consumption by an individual user. In an example, the conversion step 280 can include converting the drug coated substrate into segments and forming the segments into drug delivery products or cartridges. In an example, the cartridge is constructed to maximize the surface area of the drug coated substrate available for volatilization while minimizing packaging volume of the cartridge. In an example, the cartridge can be of a generally tubular form and assume any cross-sectional shape without altering the effect of the cartridge. In an example, the cross-section shape can include, but is not limited to, a circle, a square, a hexagon, a polygon or any symmetric or non-symmetric cross-sectional profile. Other types of shapes can be employed without departing from the present subject matter.

A fourth inspection step 285 can include examination of the cartridges to ensure that the cartridges have been suitably processed. In an example, the fourth inspection step 285 can include examination of the user shapes for visual uniformity or other parameters.

A second post-processing step 290 can include packaging and labeling of the cartridges. In an example, each cartridge can be wrapped as an individual unit. In an example, individual units can be labeled for quality assurance and governmental tax purposes.

In an example, all the aforementioned steps of the process 200 can be subject to standard manufacturing control techniques.

Figure 3:
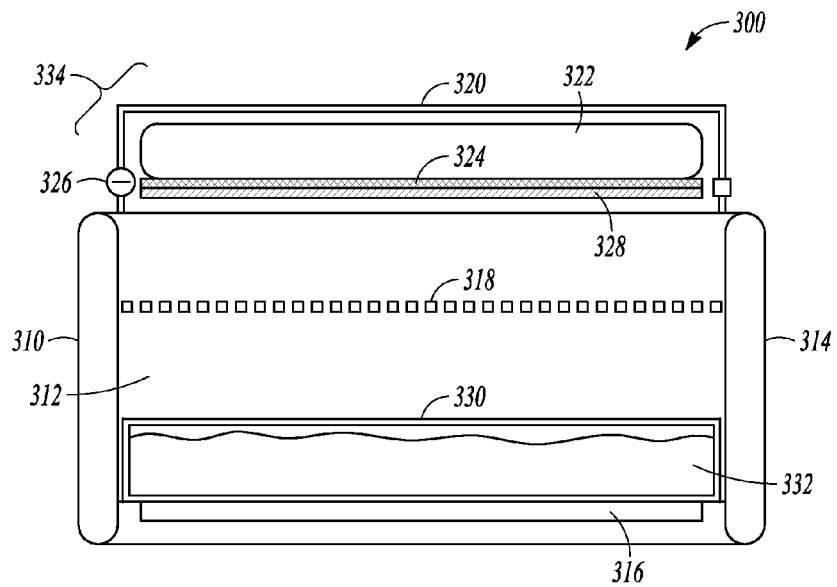
FIG. 3 is an example of a heating chamber for creating a coated substrate in accordance with the present patent application.

FIG. 3 shows an example of a heating chamber 300 of the present disclosure for use in a single sheet substrate coating process. The heating chamber 300 can include a container box 310 and a container cover 320 that can be removably attached to the container box 310. The container box 310 can include an interior surface 312, an exterior surface 314 and a controlled heat source 316 located along an interior surface 312 of the container box 310. A removable tray 330 to contain a source material 332 can be located against an interior surface 312 of the container box 310. A removable screen 318 can be located in the container box 310 between the removable tray 330 and the container cover 320 to contain source material 332.

The container cover 320 can include a hinge 326 to attach the container cover 320 to the container box 310 and a cooling bar 322 to which a substrate 324 can be located in close proximity or removably attached. In an example, the substrate 324 can be removably attached to the cooling bar 322 with clips or similar attachment aids.

The substrate 324 can be covered with a coating 328 of a drug component using, for example, a heating process. In an example, the drug component can include at least one of THC and CBD. The controlled heat source 316 can be initiated to heat the source material 332 to a selected temperature. Depending on the selected temperature, one or more chemicals can volatilize from the source material 332. The substrate 324 can be cooled through conduction (when in contact with the cooling bar 322) or radiation (when located in close proximity to the cooling bar 322) and the vapors generated during the heating process can condense onto the substrate 324 to form a coating 328 on the substrate 324. In an example, the one or more chemicals can be absorbed within the substrate 324. In an example, the one or more chemicals can be adsorbed onto the surface of the substrate 324. As used herein, a coated substrate 334 can refer to a combination of the substrate 324 and the coating 328 formed thereon.

In an example, the heating chamber 300 can be used to extract THC and CBD in the cannabis-containing composition. Using the steps above, the desirable components, THC and/or CBD, can be extracted and purified from the cannabis-containing composition by controlling the temperature in the heating chamber. As described further below, various drug coated substrates can be formed that have both THC and CBD, only THC, or only CBD, in purified form, and contain minimal to no undesirable components.

THC can volatilize in the heating chamber 300 before CBD based on volatilization temperatures of THC and CBD. Depending on a temperature that the cannabis-containing composition is heated to, THC can volatilize or THC and CBD can both volatilize. A rate of volatilization of each of THC and CBD can depend, in part, on the heating temperature and other conditions in the heating chamber 300, such as, for example, pressure. An exact temperature at which each of THC and CBD can volatilize is not necessarily precisely known and can depend, for example, on the surrounding conditions. In an example, a temperature of approximately 150-160° C. can be sufficient to volatilize THC and a temperature of approximately 180-200° C. can be sufficient to volatilize CBD.

A composition of the coated substrate 334, including a purity of the drug component, can be a function of the source material used in the heating process. In an example, the grade of cannabis used as the source material, such as the species and source of supply, can influence the composition of the coated substrate 334, including varying levels of THC and CBD. In an example, the pre-processing of the source material, such as the size of particle resulting from shredding and chopping of the source material, can influence the composition of the coated substrate 334. In an example, sampling can be performed on the source material to determine a composition of the source material. Specification parameters and standard processing control can be implemented for monitoring and controlling the composition of the source material and the coated substrate 334.

The composition of the coated substrate 334 can be a function of the control parameters used in the heating process. In an example, the temperature of the chamber, the total time the source material is exposed to the temperature of the chamber and the temperature of the cooling bar 324 can influence the coated substrate 334. In an example, these and other process parameters can be under standard processing control.

The substrate 324 can be constructed from any naturally-occurring material or any man-made material, such as an FDA-approved polymer for the delivery of drugs, or any combination of naturally-occurring or man-made materials.

The substrate 324 can be a pharmaceutically acceptable material or combination of materials, including natural and/or synthetic materials, which can capture the one or more chemicals in the drug component, such as, for example, THC or CBD. In an example, pharmaceutically acceptable materials for the substrate can include, but are not limited to, cellulosic materials, synthetically altered cellulosic materials, synthetic polymers, natural polymers or any material approved for pharmaceutical use by the United States Food and Drug Administration (FDA). In an example, the materials can be porous, micro-porous, adsorptive, absorptive or include a combination of adsorptive and absorptive properties. In an example, the substrate can be stable and non-degrading at temperatures well above the volatilization temperatures of THC and CBD. In an example, the substrate 324 can comprise an aluminum or aluminum alloy.

Figure 4:
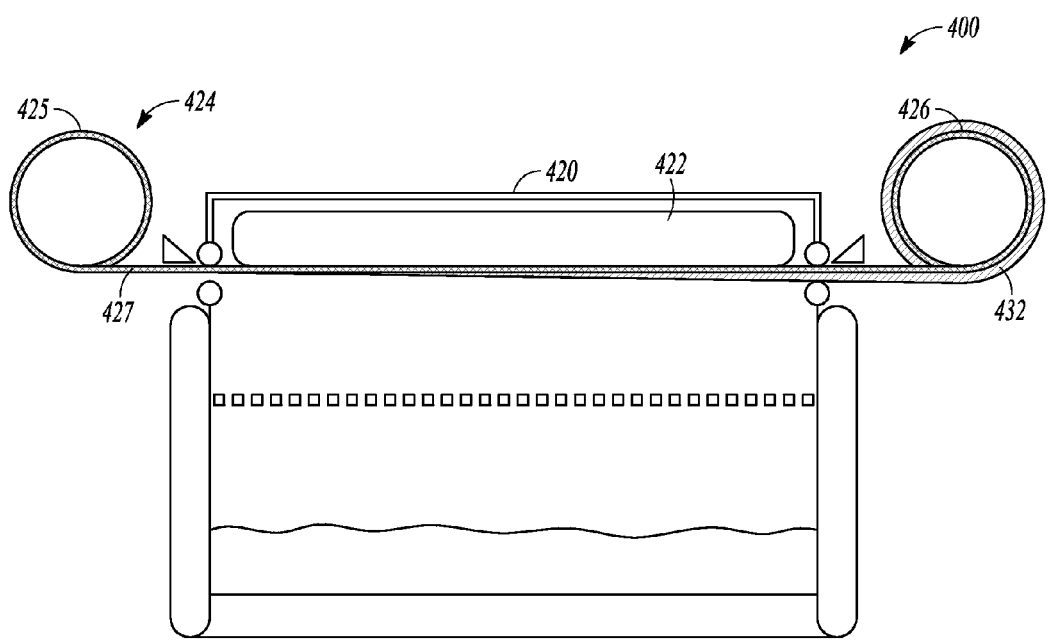
FIG. 4 is an example of a heating chamber having a continuous substrate coating process in accordance with the present patent application.

FIG. 4 shows an example of a heating chamber 400 of the present disclosure for use in a continuous sheet substrate coating process. The heating chamber 400 can include many of the same elements as the heating chamber 300 of FIG. 3, but instead of being a patch process can include additional features to enable a continuous process. The container cover 420 can include a roller take-up mechanism 424. In an example, the roller take-up mechanism 424 can include a source spool mechanism 425, a receiving spool mechanism 426 and a flexible substrate 427 extending from the source spool mechanism 425 to the receiving spool mechanism 426 and located in close proximity to the cooling bar 422. In an example, the source spool mechanism 425 can include a spindle and bearings to support the source spool and a motor attached to the source spool for tensioning of the flexible substrate 427. In an example, the receiving spool mechanism 426 can include a spindle and bearings to support the receiving spool and a motor attached to the receiving spool to draw the flexible substrate 427 across the cooling bar 422. During the heating process, the receiving spool mechanism 426 can draw the flexible substrate 427 across the cooling bar 422 so that the one or more chemicals condenses on one side of the flexible substrate 427 to form a continuous coating 432 on the flexible substrate 427.

In an example, the roller take-up mechanism 424 can be controlled to perform continuous deposition processing of the flexible substrate 427. In an example, the roller take-up mechanism 424 can be controlled to perform multi-batch deposition processing of the flexible substrate 427. Other designs can be used as an alternative to or in addition to the mechanisms 424 and 426 for enabling a continuous process.

Figure 5:
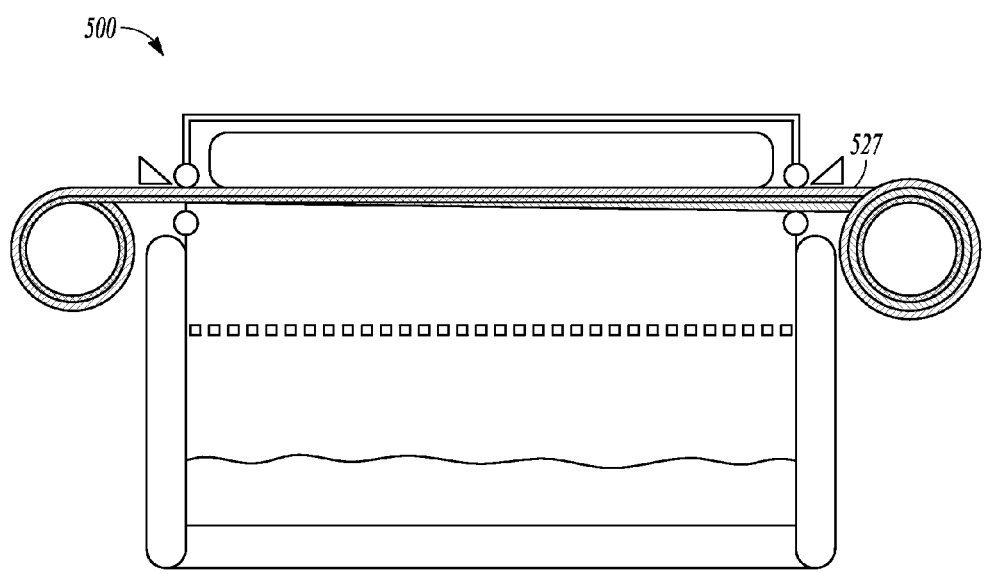
FIG. 5 is an example of a heating chamber having a double-sided, continuous substrate coating process in accordance with the present patent application.

FIG. 5 shows an example heating chamber 500 of the present disclosure for use in a double-sided, continuous sheet substrate coating process. The heating chamber 500 can include many of the same elements as the heating chambers 300 and 400 of FIGS. 3 and 4, respectively. In an example, after one side of the flexible substrate 527 has been coated in either a multi-batch or continuous deposition process, the uncoated side of the flexible substrate 527 can be subsequently coated by a multi-batch or continuous deposition process.

Figure 6:
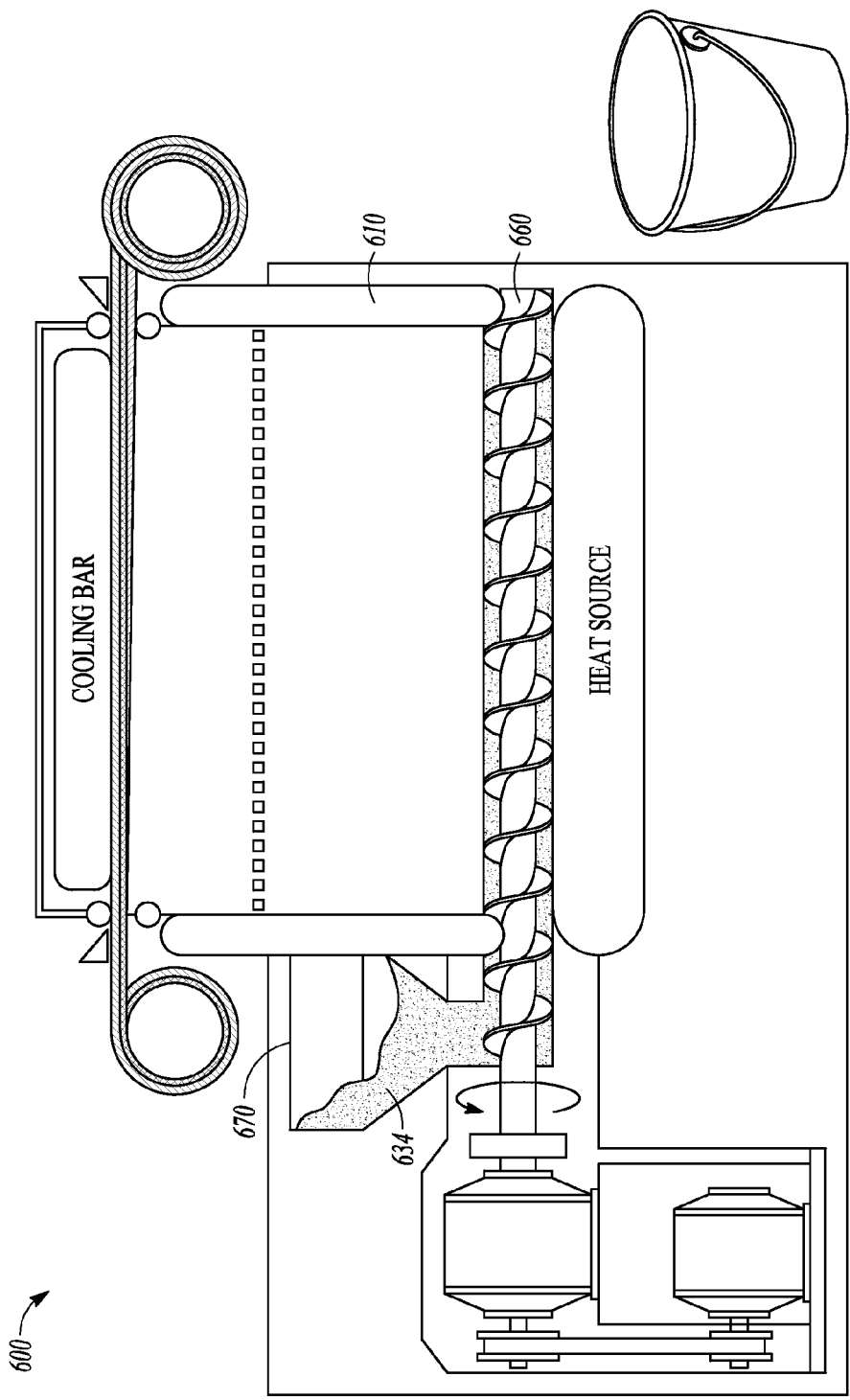
FIG. 6 is an example of a heating chamber having a double-sided, continuous substrate coating process with a source material feed system in accordance with the present patent application.

FIG. 6 shows an example heating chamber 600 of the present disclosure for use in a double-sided, continuous sheet substrate coating process with a continuous source material feed system. In an example, a screw conveyor 660 can move source material 634 into the container box 610 for heating and volatilization. In an example, the source material 634 can be deposited into a hopper 670 to supply the screw conveyor 660.

In an example, any of the heating chambers described above can be part of a mobile process such that the purification and coating processes can be done at or near the origin of the source material. In an example in which the source material is raw cannabis, the purification and coating processes can be contained or stored within a transportation device such that these steps can be performed at or near where the raw cannabis is grown.

In an example, a batch process similar to the heating chamber 300 of FIG. 3 can be used to sample source material and determine its composition, to determine, for example, levels of THC and CBD in the source material.

The heating chambers and processes described above in reference to FIGS. 3-6 are an example of a separation process for separating one or more components from the cannabis-containing composition. Other known processes may be used, such as, for example, a fractional distillation process. The particular process used for separating the desired components from the source material can depend, in part, on the composition and form (solid, liquid, etc.) of the source material, the volume of coated substrate to be produced, the time for production, technical expertise of the users, equipment availability and budget, and the cost of implementation.

By starting with raw cannabis or a cannabis-containing composition, one or more components can be extracted from the cannabis and purified by volatilizing the one or more components and coating the one or more components onto a substrate. Isolation and purity of the one or more components can be controlled through the volatilization and coating steps. The coated substrate can include more than one coating layer. In an example, a CBD rich layer can be coated over a THC rich layer. In an example, a THC rich layer can be coated on one side of the substrate and a CBD rich layer can be coated on the other side of the substrate. In an example, a CBD rich layer and minimal to no THC can be coated onto a substrate. In an example, a THC rich layer and minimal to no CBD can be coated onto a substrate. In an example, multiple substrates, each having one or more coating layers, can be used together to provide one or more drug components.

In an example, the purification and coating processes described above can include replenishing or replacing the source material after a period of time in order to vaporize an additional amount of the one or more components. In an example, the purification and coating processes described above can include processing the coated substrate into smaller pieces to increase a total surface area and then heating the pieces of coated substrate such that the at least one of THC and CBD in the coated substrate are vaporized and then condensed onto a new substrate. This can be used to further purify the at least one of THC and CBD in the coated substrate and can be repeated until a desired purity of the at least one of THC and CBD is achieved.

The heating chambers described above can be used to heat the cannabis-containing composition to any given temperature. The particular temperature or temperature range selected can depend on multiple factors, including, for example, a particular composition of the raw cannabis or the desired composition of the coated substrate. In an example, the heating chamber can be configured to heat the cannabis-containing composition to a temperature ranging between approximately 90-200° C. The temperature can be incrementally increased starting, for example, at approximately 50° C. In an example, a process for forming the coated substrate can include such a step-wise temperature increase, for example at increments of 10° C., using fractional distillation. Samples can be collected of the vapors after deposition, at all or some of the temperature intervals, to analyze the fractions and determine the composition of the coating. Based on the results, the temperature range sufficient for volatilization can be determined or adjusted based on the desired composition of the coating. It is recognized that the temperature range can depend on the starting material and how tightly the composition of the coating is to be controlled. The composition of the starting material can vary from batch to batch and can depend, for example, on where and how the raw cannabis is grown, and cleaning of the raw cannabis, or other preparation steps, prior to processing.

Given a differential of the volatilization temperatures of THC and CBD, different approaches can be used to isolate THC from CBD and vice-versa. In an example, the cannabis-containing composition can be heated to approximately 150-160° C. to volatilize THC and form a coated substrate that is rich in THC. In an example, the cannabis-containing composition can be heated to a temperature of approximately 175-190° C. to volatilize THC and CBD simultaneously. In such an example, a particular composition of the coated substrate obtained can depend, in part, on the exact temperature selected, as well as the starting ratios of THC and CBD in the cannabis-containing composition. It is recognized that other temperature ranges can be used that are sufficient for volatilizing one or both of THC and CBD.

In an example, if a coated substrate rich in CBD and not THC is desired, a two step process can be used. In a first step, the cannabis-containing composition can be heated to a first temperature sufficient to volatilize THC, but little to no CBD. Thus the coating deposited on a first substrate can be rich in THC. Depending on a length of heating in the first step, little to no THC can remain in the cannabis-containing composition after the first step is complete. In a second step, the cannabis-containing composition can be heated to a second temperature greater than the first temperature and sufficient to volatilize CBD. CBD can then be deposited onto a second substrate to form a coating rich in CBD. In other examples, the THC rich layer and the CBD rich layer can be coated as first and second coatings on a single substrate.

It may be desirable not to heat the cannabis-containing composition above a particular temperature in order to avoid volatilization of other undesirable components in addition to THC and CBD that are present in and able to volatilize from the cannabis-containing composition. In an example, a maximum heating temperature can be approximately 190-200° C. to avoid or minimize volatilization of these other components.

As described above, further processing can be performed on one or both of the first and second coated substrates to further increase a purity of the CBD or THC in the coating. Depending on the particular temperature selected, as well as the composition of the source material and other conditions in the heating chamber, the coated substrate can have varying ratios of THC to CBD.

An amount of the one or more drug components in the coated substrates can be determined as part of the process for forming the coated substrate and the drug delivery cartridges described below. As described above, process control methods can be implemented to control, for example, a thickness of the coating on the substrate. Based on sampling of the source material, a composition of the coating on the substrate can also be determined. Other known techniques can be used to determine a composition of the coating on the substrate. As such, an amount of the one or more drug components, such as, for example, THC and CBD, can be determined per unit area of the coated substrate. This can be used to determine a surface area of the drug delivery cartridge if there is a specified level of the one or more drug components in the drug delivery cartridge. Similarly, if the surface area of the drug delivery cartridge is specified, the thickness of the coating on the substrate can be adjusted in order to meet a specified level of the one or more drug components in the drug delivery cartridge. The methods described herein for forming the coated substrates and the drug delivery cartridges can be used to effectively and accurately determine a composition and level of the one or more drug components, which can be used for dosage control.

Coated substrates as described herein containing one or more drug components can be used to form a three-dimensional structure configured for use as a drug delivery product. In an example, a coated substrate can be used as a drug delivery cartridge in a delivery device. As used herein, a drug delivery cartridge can refer to a replaceable element in a drug delivery system that is slowly depleted of one or more drug components as a consequence of continued use or intervals of use. The drug delivery cartridge can be replaced for continued use of the drug delivery system. In an example, drug delivery cartridges can be designed to maximize surface area exposed to an air flow while minimizing package volume.

Coated substrates can take many structural forms. In an example, coated substrates can include, but are not limited to, cubes, cones, parallelepipeds, or other three-dimensional shapes. In an example, a coated substrate can be in the form of a sheet. As used herein, a sheet can be any three-dimensional structure defined by a first dimension, a second dimension and a third dimension where the first dimension is much smaller than the second and third dimensions. In an example, a sheet can be generally rectangular in shape with a first end and a second end opposite the first end.

Figure 7A:
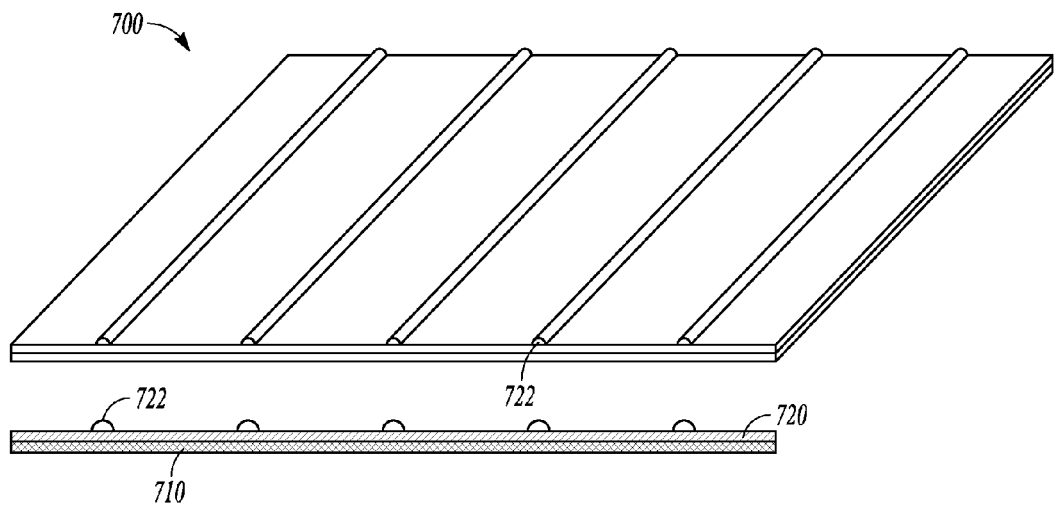
FIG. 7A is an example of a drug coated substrate in accordance with the present patent application.

FIG. 7A shows an example of a drug coated substrate 700 of the present disclosure which can be formed using the techniques described above or generally known in the art for extracting and purifying one or more drug components and coating the one or more drug components on a substrate. The drug coated substrate 700 can include a substrate component 710, a drug component 720 coated on the substrate component 710 and spacers 722 located on the substrate component 710 or the drug component 720. In an example, the spacers 722 can be located on the substrate component 710 before the substrate component 710 is coated. In an example, the spacers 722 can be located on the drug component 720 after the substrate component 710 is coated.

Figure 7B:
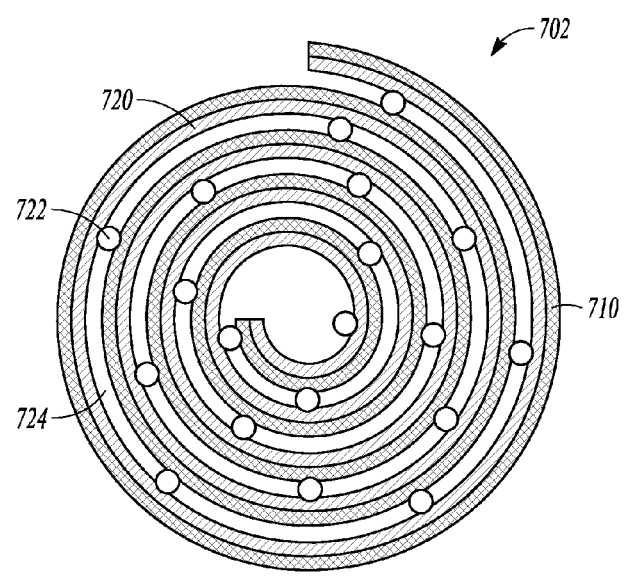
FIG. 7B is an example of a drug delivery cartridge formed from the drug coated substrate of FIG. 7A, in accordance with the present patent application.

FIG. 7B shows an example where the drug coated substrate 700 can be converted into a three-dimensional structure configured for use as a drug delivery cartridge 702. In an example, the drug coated substrate 700 can be rolled into a spirally wound cylindrical shape to form the drug delivery cartridge 702. In an example, the plurality of spacers 722 can be used as a structural element to maintain a channel 724 between layers of the drug delivery cartridge 702 to allow for the passage of heated air. The drug delivery cartridge 702 can include any number of layers.

The drug delivery cartridge 702 can be used with a drug delivery device, an example of which is described below and shown in FIG. 7. In an example, the drug delivery device can include, but is not limited to a vaporizer, an e-cigarette, a bong or a water pipe. Alternatively, the drug delivery cartridge 702 can be used by directly applying heated air to the drug delivery cartridge 702 to volatilize the drug from the drug delivery cartridge 702. In an example, heated air can be directly applied to the drug delivery cartridge 702 by any heating process or heating device that can include, but is not limited to, an e-cigarette, a bong, a water pipe and a vaporizer device. In an example, heated air can be directed through the channel 724 to volatilize the drug from the drug delivery cartridge 702.

Figure 8:
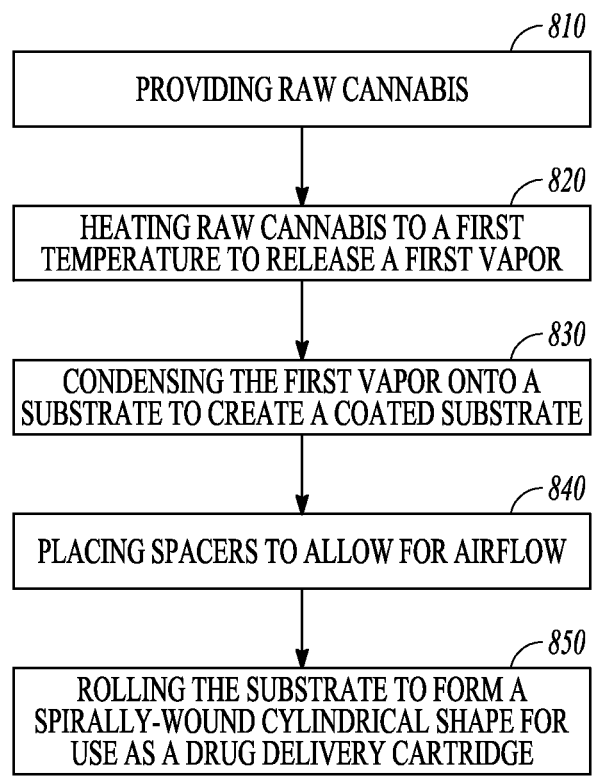
FIG. 8 is a block diagram of an example of a process to construct a drug delivery cartridge having a spirally wound cylindrical shape, in accordance with the present patent application.

FIG. 8 shows a flow chart of an example process to construct a spirally wound cylindrical shape, similar to the cartridge 702 of FIG. 7B. In an example, step 810 can include providing a supply of raw cannabis; step 820 can include heating the raw cannabis to a first temperature to release a first vapor; step 830 can include condensing the first vapor onto a substrate to create a coated substrate; step 840 can include placing spacers on the coated substrate to allow for airflow through the cartridge; step 850 can include rolling the coated substrate to form a spirally-wound cylindrical shape configured for use as a drug delivery cartridge.

Figure 9:
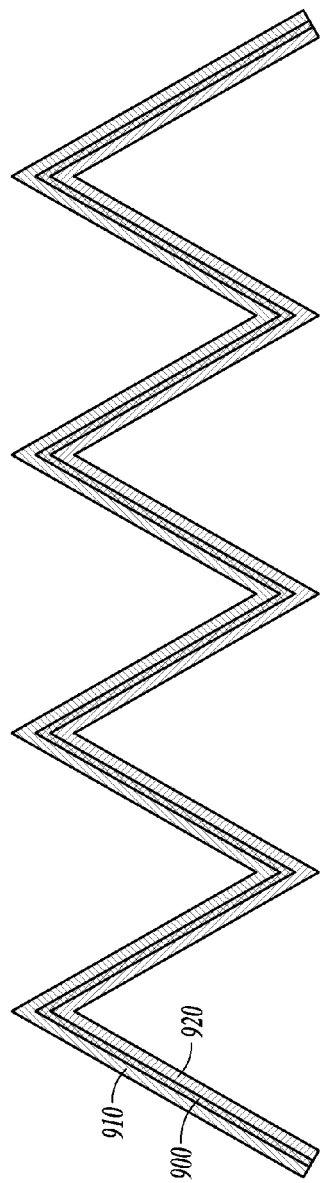
FIG. 9 is an example of a drug delivery cartridge in accordance with the present patent application.

FIG. 9 shows an example of a coated substrate shaped in a saw-tooth, zig-zag, or accordion configuration. In an example, the saw-tooth coated substrate 900 includes a first coating 910 where the first coating 910 can be one of THC or CBD. In an example, the saw-tooth coated substrate 900 includes a second coating 920 where the coating 920 can be one of THC or CBD.

Figure 10:
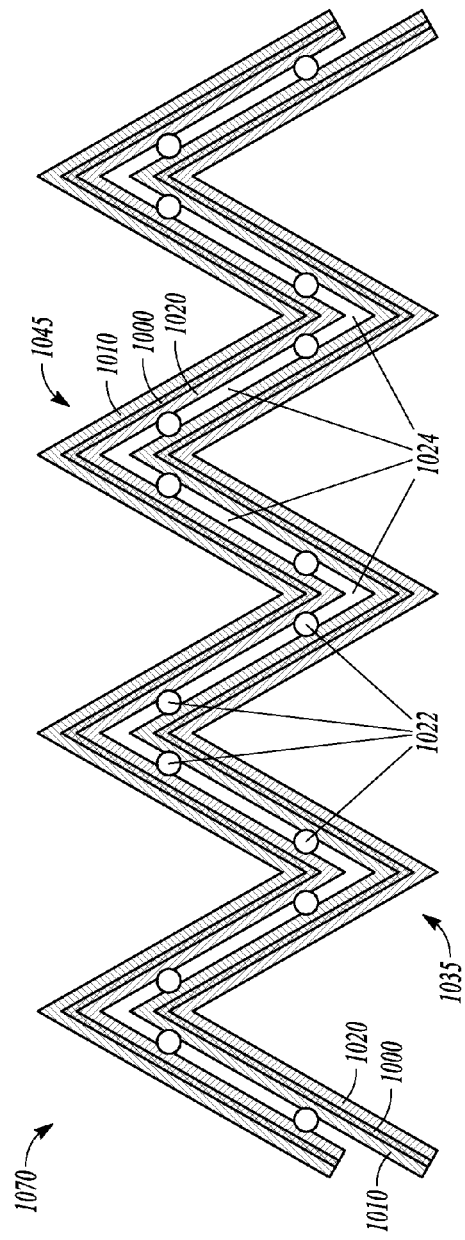
FIG. 10 is an example of a drug delivery cartridge having multiple layers of coated substrates, in accordance with the present patent application.

FIG. 10 shows an example of a two-substrate assembly 1070 where a first saw-tooth coated substrate 1035 and a second saw-tooth coated substrate 1045 can be stacked for use as a drug delivery cartridge. In an example, a plurality of spacers 1022 can be used as structural elements to maintain a plurality of channels 1024 between the first saw-tooth coated substrate 1035 and the second saw-tooth coated substrate 1045 to allow for the passage of heated air. In an example, the two-substrate assembly 1070 can be stacked so that the first coating 1010 of the first saw-tooth coated substrate 1035 can face the second coating 1020 of the second saw-tooth coated substrate 1045. In an example, a plurality of two substrate assembly 1070 can be stacked for use as a drug delivery cartridge.

Figure 11:
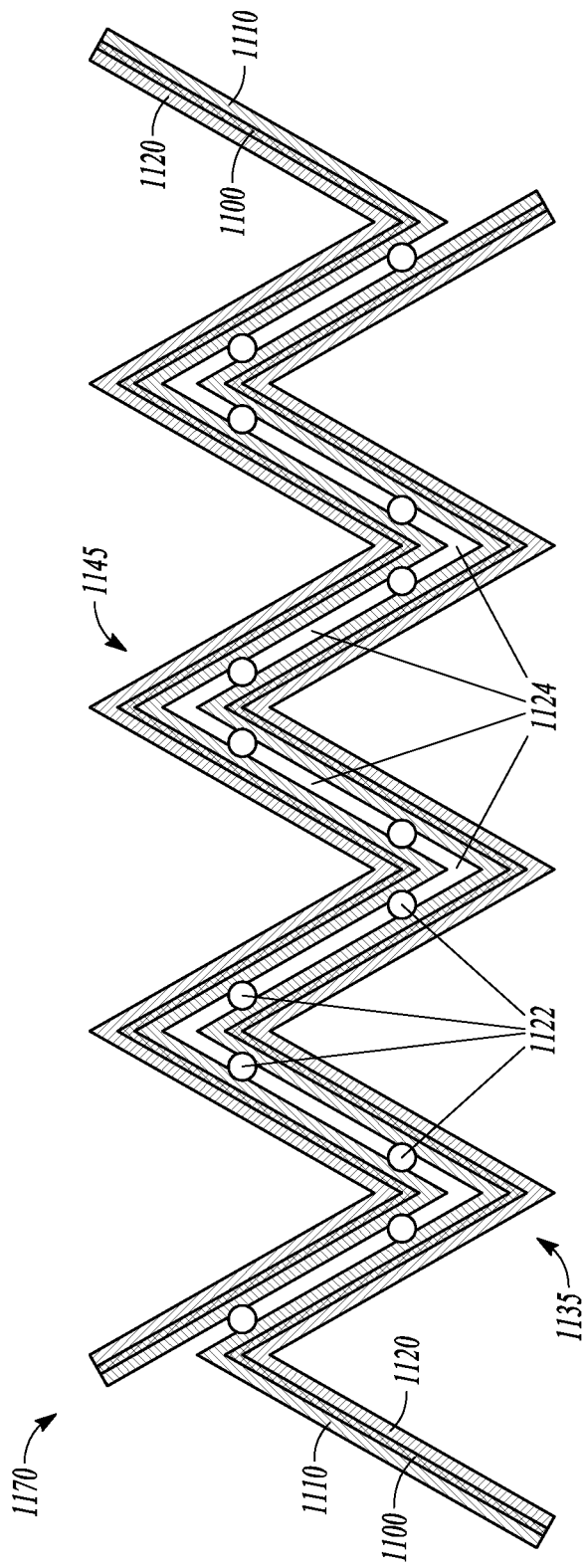
FIG. 11 is an example of a drug delivery cartridge having multiple layers of coated substrates, in accordance with the present patent application.

FIG. 11 shows an example of a two-substrate assembly 1170 where the first coating 1110 of a first saw-tooth coated substrate 1135 can face the first coating 1110 of a second saw-tooth coated substrate 1145. In an example, a plurality of two-substrate assembly 1170 can be stacked for use as a drug delivery cartridge.

Figure 12:
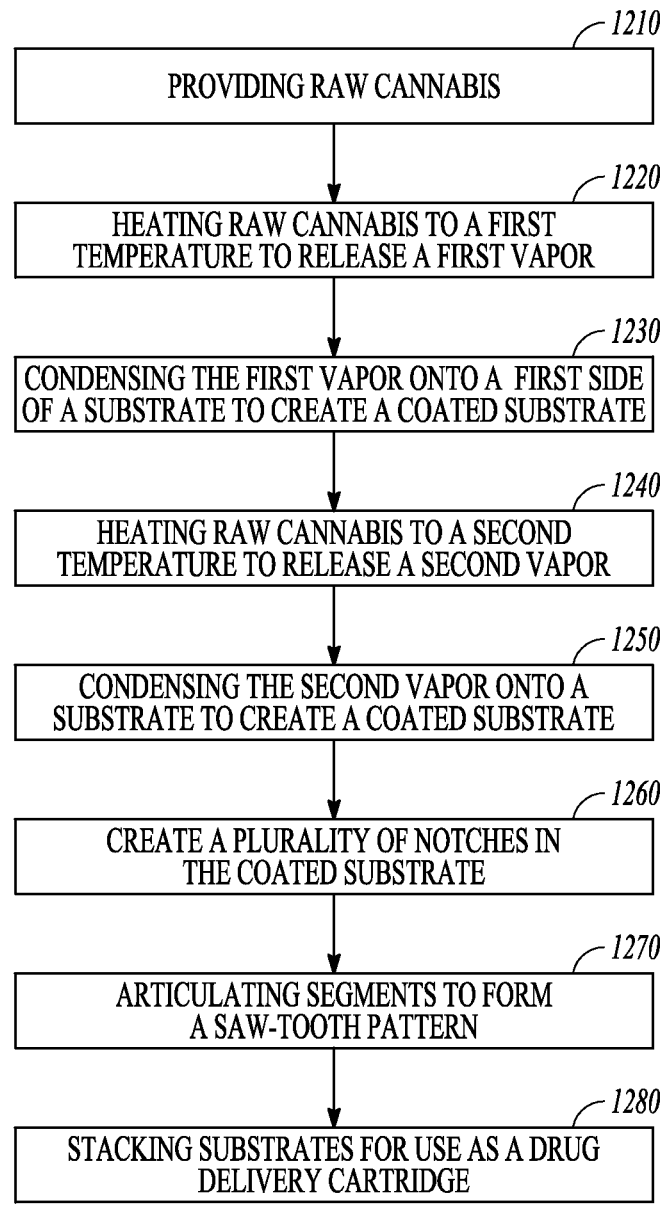
FIG. 12 is a block diagram of an example of a process to construct a drug delivery cartridge in accordance with the present patent application.

FIG. 12 shows an example of a process to construct a saw-toothed drug delivery cartridge. In an example, step 1210 can include providing a supply of raw cannabis; step 1220 can include heating the raw cannabis to a first temperature to release a first vapor; step 1230 can include condensing the first vapor onto a first side of a substrate; step 1240 can include heating the raw cannabis to a second temperature to release a second vapor; step 1250 can include condensing the second vapor onto a second side of the substrate; step 1260 can include creating a plurality of notches in the coated substrate; step 1270 can include articulating the segments to form a saw-tooth pattern and step 1280 can include stacking the substrate for use as a drug delivery cartridge. The process of FIG. 12 can be modified to incorporate the multiple substrate assemblies shown in FIGS. 10 and 11.

Figure 13A:
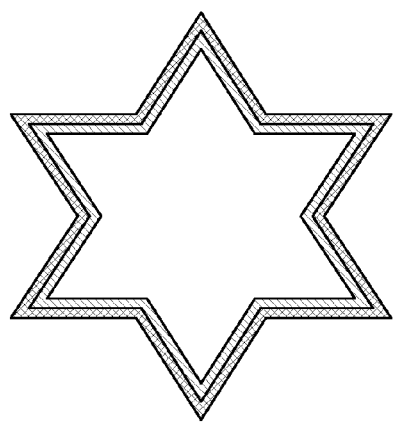
FIG. 13A is a top view of an example of a polygonal drug delivery cartridge in accordance with the present patent application.
Figure 13B:
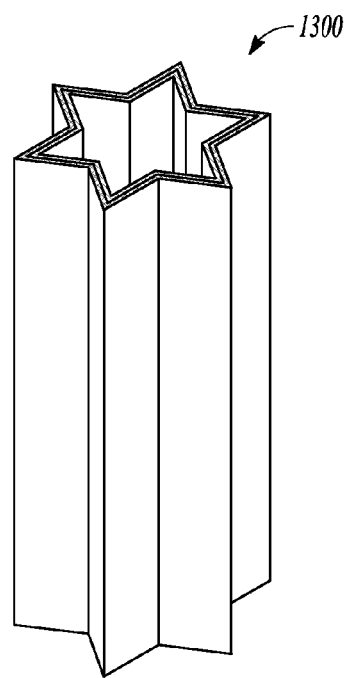
FIG. 13B is a perspective view of the polygonal drug delivery cartridge of FIG. 13A.

FIGS. 13A and 13B show top and side views, respectively, of an example of a polygonal drug delivery cartridge 1300. In an example, the cross-sectional shape of the polygonal drug delivery cartridge can include, but is not limited to, a three-side cross-section, a four-sided cross-section or an "n"-sided cross-section where "n" can be any number equal to or greater than 3.

FIG. 13C shows notches 1370 formed in the substrate 1310 and the coating 1320 that can allow a segment 1375 to articulate with respect to an adjacent segment 1375. As used herein, a segment 1375 is the portion of the substrate 1310 and coating 1320 located between two notches 1370.

Figure 14:
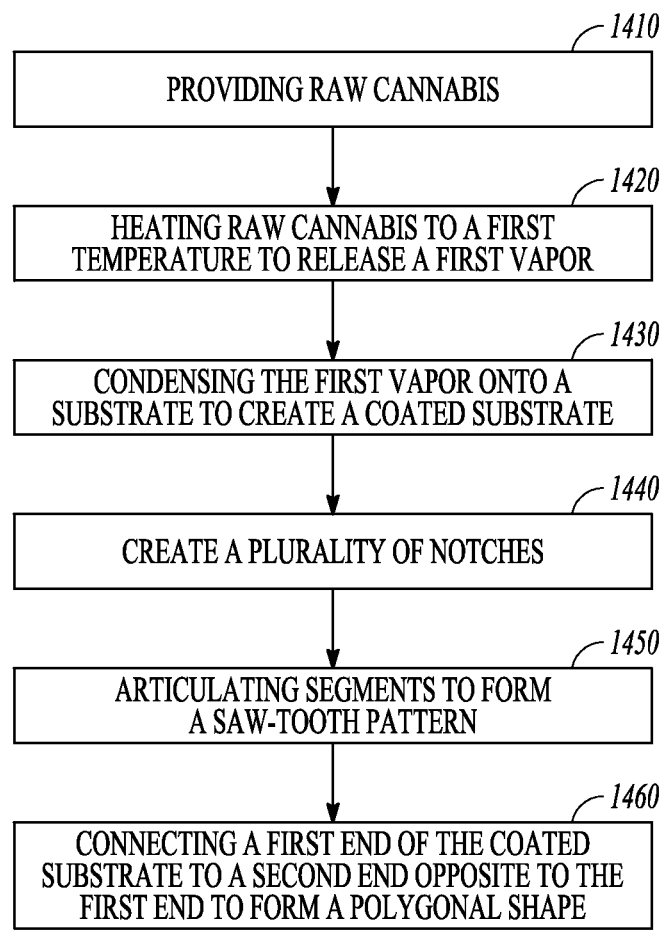
FIG. 14 is a block diagram of an example of a process to construct a polygonal drug delivery cartridge in accordance with the present patent application.

FIG. 14 shows an example of a process to construct a closed polygonal shaped drug delivery cartridge similar to the star-shaped cartridge 1300 of FIG. 13. In an example, step 1410 can include providing a supply of raw cannabis; step 1420 can include heating the raw cannabis to a first temperature to release a first vapor; step 1430 can include condensing the first vapor onto a substrate to create a coated substrate; step 1440 can include creating a plurality of notches and step 1450 can include articulating the segments to form a saw-tooth pattern; and step 1460 can include connecting the first end to the second end to form a polygonal shape. In an example, step 1460 can include manipulating the segments to align the segments in a desired orientation relative to one another.

Other shapes can be used for a drug delivery cartridge. Any of the examples described and shown in FIGS. 7B, 9, 10, 11 and 13A-13C can include additional layers of substrate and each layer of substrate can include one or more coating layers. As stated above in reference to FIG. 7B, the drug delivery cartridges described herein can be used alone or in combination with a drug delivery device. Each drug delivery cartridge can be designed such that heated air can be passed through the cartridge and one or more drug components can be volatilized and inhaled by a user.

Dimensions of any of the drug delivery cartridges described herein can depend, in part, on whether a drug delivery device is intended to be used with the cartridge and a particular design of the drug delivery device. These dimensions can include a length, width and overall shape of the drug delivery cartridge and can depend on the length and width of the coated substrate used to form the drug delivery cartridge. The dimensions of the drug delivery cartridge can also depend, in part, on an amount of the one or more drug components in the drug delivery cartridge and an intended dosage of the one or more drug components.

Figure 15:
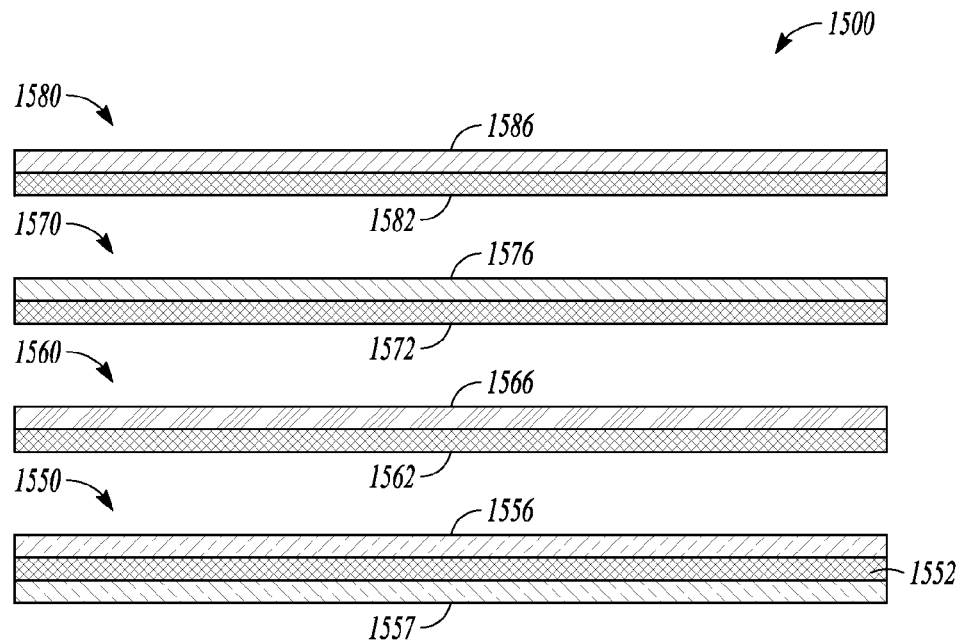
FIG. 15 is an exploded cross-section view of an example of a multi-layer substrate in accordance with the present patent application.

FIG. 15 shows an exploded view of an example of an assembly 1500 comprising multiple layers of coated substrates. In an example, an active drug layer 1550 can include a substrate 1552 with a first surface and a second surface where a THC coating 1556 can be applied to the first surface and a CBD coating 1557 can be applied to the second surface. In an example, a taste layer 1560 can include a substrate 1562 having a taste coating 1566 applied to the substrate 1562 to enhance the user ingestion experience. In an example, the taste coating 1566 can include a flavoring that can include, but is not limited to, fresh mint. In an example, an enhancement layer 1570 can include a substrate 1572 having an enhancement coating 1576 applied to the substrate 1572 where the enhancement coating 1576 can include at least a second compound that can augment the therapeutic effect of the THC or CBD. In an example, the second compound can include, for example, an opiate. In an example, an amelioration layer 1580 can include a substrate 1582 having an amelioration coating 1586 applied to the substrate 1582 where the amelioration coating 1586 can include at least a third compound that can minimize any undesirable side effects of THC or CBD, if applicable. In an example, the active drug layer 1550, the taste layer 1560, the enhancement layer 1570 and the amelioration layer 1580 can be assembled together or in any permutation. In an example, the assembly 1500 can be converted into a three-dimensional structure for use as a drug delivery cartridge as described above. In other examples, an assembly can include any number and combination of layers depending on desired properties of the assembly. In an example, spacers similar to the spacers 722 shown in FIGS. 7A and 7B can be placed between each layer prior to forming the three-dimensional structure to allow for the passage of air between the layers.

Figure 16:
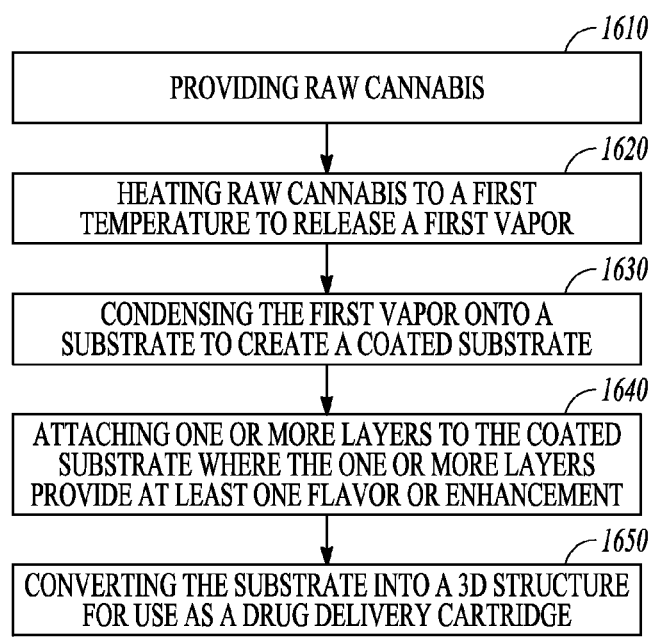
FIG. 16 is a block diagram of an example of a process used to make a drug delivery cartridge having two or more layers, in accordance with the present patent application.

FIG. 16 shows an example of a process used to make a drug delivery cartridge where the coated substrate includes two or more layers where at least one provides flavor or enhancement. In an example, step 1610 can include providing a supply of raw cannabis; step 1620 can include heating the raw cannabis to a first temperature to release a first vapor; step 1630 can include condensing the first vapor onto a substrate to create a coated substrate; step 1640 can include attaching one or more layers to the coated substrate where the one or more layers provide at least one of flavor or enhancement of the at least one of THC and CBD, and step 1650 can include converting the substrate into a three-dimensional structure for use as a drug delivery cartridge. In an example, an additional step can be performed between steps 1630 and 1640 which can include heating the raw cannabis to a second temperature to release a second vapor, thus creating a second coating on the coated substrate, as described above.

As described above in reference to the coated substrates, a composition and amount of the one or more drug components in the drug delivery cartridge can be determined and controlled, which can be used for dosage control of the drug(s). In an example, the drug delivery cartridges can contain a predetermined quantity of THC or CBD and can be designed as single dosage or multi-dosage cartridges. Using the control parameters described above, a quantity of THC or CBD in the drug delivery cartridge can vary depending, for example, on the intended use of the THC or CBD.

A drug delivery cartridge can cooperate with a drug delivery device that supplies a volatilizing heat source to deliver the one or more drug components in the drug delivery cartridge to a user. In an example, the drug delivery device can include, but is not limited to, an e-cigarette, a bong, a water pipe and a vaporizer.

Figure 17:
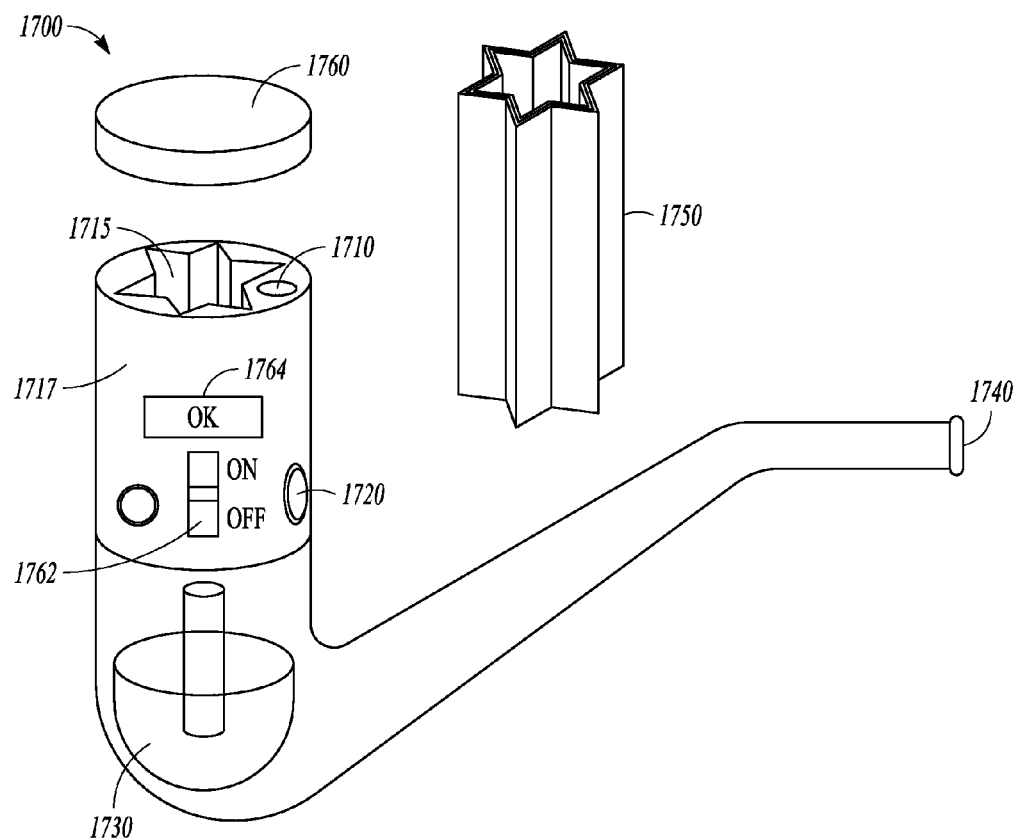
FIG. 17 is a perspective view of an example of a drug delivery cartridge in combination with a drug delivery device, in accordance with the present patent application.

FIG. 17 shows a drug delivery cartridge 1750 in combination with an example of a drug delivery device, an electronic pipe 1700. In an example, the electronic pipe 1700 and the drug delivery cartridge 1750 form a drug delivery system. The electronic pipe 1700 can include a heating element 1710 with an opening 1715 sized and shaped to receive the drug delivery cartridge 1750, a power unit 1717, an air intake 1720, a moisturizing and cooling chamber 1730, a mouthpiece 1740, a cover 1760, a power switch 1762 and a digital readout 1764.

The heating element 1710 can heat the drug delivery cartridge 1750 to a specified temperature. In an example, the heating element 1710 can pre-heat the drug delivery cartridge 1750 to a temperature less than a volatizing temperature of the drug delivery cartridge 1750 so that the drug delivery cartridge 1750 can readily volatize the coated surface on user demand. In an example, the heating element 1710 can heat the drug delivery cartridge 1750 to a temperature greater than or equal to a volatizing temperature of the one or more drug components to volatize the drug component(s) for delivery of the volatized drug on user demand.

The air intake 1720 provides makeup air to the electronic pipe 1700. In an example, the air intake 1720 can be a hole located in the electronic pipe 1700 in communication with the opening 1715, the moisturizing and cooling chamber 1730 and the mouthpiece 1740. In an example, the air intake 1720 can allow makeup air to flow into the electronic pipe 1700 when a user induces a negative pressure (or suction) action at the mouthpiece 1740.

The cover 1760 can prevent users from contacting the heating element 1710 during operation of the electronic pipe 1700. In an example, the cover 1760 removably attaches to the electronic pipe 1700 to prevent loss of the drug delivery cartridge 1750 during use.

The power switch 1762 controls the flow of electrical power from a power unit 1717 to the heating element 1710. In an example, electrical power can flow from the power unit 1717 to the heating element 1710 when the power switch 1762 is in an 'on' position. In an example, electrical power can be prevented from flowing from the power unit 1717 to the heating element 1710 when the power switch 1762 is in an 'off' position.

The drug delivery cartridge 1750 can be used with the electronic pipe 1700 to deliver a predetermined and accurate quantity of volatized drug to a user. As described above, the amount of the one or more drug components in the cartridge 1750 can be controlled and thus known. The cartridge 1750 can be a single dose cartridge or intended for use over multiple doses. In an example, a user can remove the cover 1760 from the electronic pipe 1700 and insert a drug delivery cartridge 1750 into the opening 1715. In an example, the user can removably attach the cover 1760 to the electronic pipe 1700 before adjusting the power switch 1862 to the 'on' position in order to preheat the drug delivery cartridge 1750. In an example, the user can monitor the digital display 1764 for a visual cue that indicates that the electronic pipe 1700 is ready for use.

A drug delivery device can be configured to control the dosage of the drug to the user such that a multi-dose cartridge can be used with the drug delivery device, while still maintaining dosage control. For example, a drug delivery device similar to the electronic pipe 1700 can be configured to deliver a predetermined amount of drug per inhalation.

The drug delivery device can control how much air passes through the drug delivery cartridge and how much air is delivered to the user. In an example, a valve device inserted into the air flow of the drug delivery device can be used to control the volume of air available to the user. For example, the valve device can be located in the mouthpiece of a drug delivery device to throttle the volume of air flowing through the mouthpiece. In an example, the valve device can include, but is not limited to, a flapper valve, a ball valve, a gate valve, a butterfly valve, a duckbill valve or an adjustable orifice.

In an example, the valve device can include a timer device that can cause the valve device to open or close after an interval of time to regulate air flow through the drug delivery device. For example, the valve device can include an open-loop timer device utilizing mechanisms such as a spring or a mechanical linkage to open or close the valve device. In another example, the valve device can include a closed-loop timer device using an actuator, an electrical control circuit and one or more feedback sensors to implement a control algorithm to open and close the valve.

The drug delivery device can also control other parameters that impact the amount of drug(s) delivered to the user, including, for example, a temperature that the cartridge is heated to and the rate of airflow. Because the drug delivery cartridge only contains the desired components, for example, CBD or THC, which have already been separated from the undesirable components in the source material, sufficient heat can be applied to the drug delivery cartridge to quickly vaporize the drug(s) without worrying about the undesirable components also being vaporized.

The drug delivery cartridge can be configured to control the amount or dose of drug delivered. In an example, the drug delivery cartridge can be coated with a micro porous film to control the flow of drug vapor from the drug delivery cartridge. For example, the diameter of the pores in the micro porous film applied to the coated substrate can be sized to control the dose of drug delivered. In an example, the coated substrate used to form a drug delivery cartridge can be coated with a micro porous film to control the flow of drug vapor from the coated substrate and thereafter formed into a drug delivery cartridge.

In an example, the drug delivery cartridge can be constructed from a coated substrate comprising a conductive material. In an example, the conductive material can include, but is not limited to, aluminum. In an example, an electrical power circuit can be connected to the conductive material to resistively heat the conductive material to a temperature sufficient to volatilize the drug on the coated substrate. In an example, the electrical power circuit can include an electrical control circuit and one or more feedback sensors to resistively heat the conductive material to a sufficient temperature and thereafter accurately maintain the temperature over a period of time.

In an example, the drug delivery cartridges described herein can be used with a vaporizer. The vaporizer can be configured to include a chamber or receptacle that the drug delivery cartridge can be placed in. The drug delivery cartridge can be configured as a single dose or multi-dose cartridge. Given the control parameters that can be used in the process of making the drug delivery cartridge, the drug delivery cartridge can include a known quantity of the drug component(s). As similarly stated above, a heating temperature of the vaporizer is not a significant concern because the drug delivery cartridge only includes the desired components and the substrate used in forming the drug delivery cartridge can be inert at these operating temperatures.

The above detailed description includes references to the accompanying drawings, which form a part of the detailed description. The drawings show, by way of illustration, specific embodiments in which the invention can be practiced. These embodiments are also referred to herein as "examples." Such examples can include elements in addition to those shown or described. However, the present inventor also contemplates examples in which only those elements shown or described are provided. Moreover, the present inventor also contemplates examples using any combination or permutation of those elements shown or described (or one or more aspects thereof), either with respect to a particular example (or one or more aspects thereof), or with respect to other examples (or one or more aspects thereof) shown or described herein.

All publications, patents, and patent documents referred to in this document are incorporated by reference herein in their entirety, as though individually incorporated by reference. In the event of inconsistent usages between this document and those documents so incorporated by reference, the usage in the incorporated reference(s) should be considered supplementary to that of this document; for irreconcilable inconsistencies, the usage in this document controls.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In this document, the terms "including" and "in which" are used as the plain-English equivalents of the respective terms "comprising" and "wherein." Also, in the following claims, the terms "including" and "comprising" are open-ended, that is, a system, device, article, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

The above description is intended to be illustrative, and not restrictive. For example, the above-described examples (or one or more aspects thereof) may be used in combination with each other. Other embodiments can be used, such as by one of ordinary skill in the art upon reviewing the above description. The Abstract is provided to comply with 37 C.F.R. §1.72(b), to allow the reader to quickly ascertain the nature of the technical disclosure. It is submitted with the understanding that it will not be used to interpret or limit the scope or meaning of the claims. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description, with each claim standing on its own as a separate embodiment, and it is contemplated that such embodiments can be combined with each other in various combinations or permutations. The scope of the invention should be determined with reference to the appended claims, along with the full scope of equivalents to which such claims are entitled.

The claimed invention is:

1. A method of purifying at least one of tetrahydrocannabinol (THC) and cannabidiol (CBD) from a cannabis-containing composition, the method comprising:
    heating the cannabis-containing composition to a first temperature to volatilize at least one of THC and CBD into a first vapor; and
    condensing the first vapor onto an electrically conductive substrate to form a first coating, the first coating comprising at least one of THC and CBD, wherein the coated substrate is configured for conversion to a three-dimensional structure for use as a drug delivery cartridge.

2. The method of claim 1 wherein the first coating comprises THC, the method further comprising:

after forming the first coating, heating the cannabis-containing composition to a second temperature to volatilize CBD into a second vapor, wherein the second temperature is greater than the first temperature; and condensing the second vapor onto the substrate to form a second coating over the first coating, the second coating comprising CBD.

3. The method of claim 1 wherein the substrate includes a first side and a second side and the first coating is formed on the first side of the substrate and comprises THC, and the method further comprising:

heating the cannabis-containing composition to a second temperature to volatilize CBD into a second vapor, the second temperature greater than the first temperature; and condensing the second vapor onto the second side of the substrate to form a second coating, the second coating comprising CBD.

4. The method of claim 1 wherein the first coating comprises THC, the method further comprising:

after forming the first coating, heating the cannabis-containing composition to a second temperature to volatilize CBD into a second vapor, the second temperature greater than the first temperature; and condensing the second vapor onto a second substrate to form a coating comprising CBD.

5. The method of claim 1 wherein the first temperature is equal to or greater than a temperature sufficient to volatilize CBD, and the first coating comprises THC and CBD.

6. The method of claim 1 wherein condensing the first vapor onto a substrate includes placing the substrate on or near a cooling bar.

7. The method of claim 1 wherein the cannabis-containing composition is raw cannabis.

8. The method of claim 7 further comprising:
processing the raw cannabis into smaller pieces prior to heating the raw cannabis.

9. A method of concentrating at least one of tetrahydrocannabinol (THC) and cannabidiol (CBD) from a cannabis-containing composition, the method comprising:

(a) heating the cannabis-containing composition to a first temperature to volatilize at least one of THC and CBD into a first vapor;
(b) condensing the first vapor onto a substrate to form a first coating comprising at least one of THC and CBD;
(c) processing the substrate into substrate pieces thereby increasing a total surface area of the processed substrate;
(d) heating the substrate pieces to the first temperature to volatize at least one of THC and CBD into a second vapor; and
(e) condensing the second vapor onto a second substrate to form a second coating comprising at least one of THC and CBD, wherein a weight fraction of the at least one of THC and CBD in the second coating is greater than the weight fraction of the at least one of THC and CBD in the first coating.

10. The method of claim 9 further comprising: repeating steps (c)-(e) until the weight fraction of the at least one of THC and CBD in the subsequent coating exceeds a specified level.

11. A method of making a drug delivery cartridge, the method comprising:

heating a cannabis-containing composition to a first temperature to volatize at least one of tetrahydrocannabinol (THC) and cannabidiol (CBD) into a first vapor;

condensing the first vapor onto a substrate to form a coating on the substrate comprising at least one of THC and CBD; and converting the coated substrate into a three-dimensional structure configured for use as a drug delivery cartridge.

12. The method of claim 11 wherein converting the coated substrate includes rolling the coating substrate to form a spirally-wound cylindrical shape.

13. The method of claim 12 wherein a plurality of spacers are placed along the coated substrate prior to converting, the plurality of spacers configured to allow for airflow through the spirally-wound cylindrical shape.

14. The method of claim 11 wherein the coated substrate comprises a first end and a second end opposite to the first end, the method further comprising:

creating a plurality of notches at multiple locations on the coated substrate between the first and second ends, wherein the notches create an interface and an interval between adjacent notches defines a segment of coated substrate; and bending the segments relative to one another at the interfaces so as to form a saw-tooth pattern.

15. The method of claim 14 further comprising:
connecting the first end to the second end to form a closed polygonal shape.

16. The method of claim 11 further comprising:
ascertaining an average amount of at least one of THC and CBD in the coating per unit area of the coated substrate.

17. The method of claim 16 wherein converting the coated substrate into a three-dimensional structure includes determining a total area of the coated substrate to use for the three-dimensional structure based on a predetermined amount of the at least one of THC and CBD in the drug delivery cartridge.

18. The method of claim 11 further comprising:
attaching one or more layers to the coated substrate prior to converting the coated substrate into a three-dimensional structure, the one or more layers configured to provide at least one of flavor or enhancement of the at least one of THC and CBD.

19. The method of claim 11 further comprising:
heating the cannabis-containing composition to a second temperature greater than the first temperature to volatilize CBD into a second vapor prior to converting the coated substrate into a three-dimensional structure; and
condensing the second vapor onto the substrate to form a second coating on the substrate, the second coating comprising CBD.

20. The method of claim 11 wherein the first temperature is equal to or greater than a temperature sufficient to volatilize CBD and the first coating comprises THC and CBD.

21. The method of claim 1, wherein the substrate comprises aluminum.

* * * * *